United States Patent [19]

Suroff

[11] Patent Number: 4,991,249
[45] Date of Patent: Feb. 12, 1991

[54] ULTRASONIC TOOTHBRUSH

[76] Inventor: Leonard W. Suroff, 12 Tompkins Ave., Jericho, N.Y. 11753

[21] Appl. No.: 308,798

[22] Filed: Feb. 9, 1989

[51] Int. Cl.⁵ .............................................. A46B 13/02
[52] U.S. Cl. .................................. 15/22.2; 15/176.2; 403/348; 433/119; 433/127
[58] Field of Search ................... 15/22 R, 145, 176.2; 81/489; 433/118, 119, 127; 403/348, 349

[56]  References Cited

U.S. PATENT DOCUMENTS

| | | | |
|---|---|---|---|
| 1,675,873 | 7/1928 | Bauer | 433/127 |
| 2,709,227 | 5/1955 | Foley et al. | 15/22 R X |
| 3,369,265 | 2/1968 | Halberstadt et al. | 15/22 R |
| 3,510,747 | 5/1970 | Petrides | 15/22 R |
| 3,840,932 | 10/1974 | Balamuth et al. | 15/22 R |
| 3,980,906 | 9/1976 | Kuris et al. | 15/22 R |
| 4,192,035 | 3/1980 | Kuris | 15/22 R |
| 4,333,197 | 6/1982 | Kuris | 15/22 R |
| 4,668,119 | 5/1987 | Galletti | 403/349 |

FOREIGN PATENT DOCUMENTS

889135  9/1953  Fed. Rep. of Germany ..... 15/176.2

Primary Examiner—Edward L. Roberts
Attorney, Agent, or Firm—Sachs & Sachs

[57]  ABSTRACT

An ultrasonic toothbrush for use in personal dental hygiene care includes an exchangeable toothbrush member which is removably attached to an ultrasonic power member and may be readily removed therefrom with less than one revolution and inserted on to the ultrasonic power member in a like manner. Provision is made for locking the toothbrush to the power member and is arranged to transfer the ultrasonic energy from the power member to the toothbrush with minimum energy loss.

39 Claims, 3 Drawing Sheets

ULTRASONIC TOOTHBRUSH

BACKGROUND OF THE INVENTION

1. Field of the Invention

The present invention relates to apparatuses for the cleaning of teeth, and more particularly, to an apparatus for personal dental care employing ultrasonic energy wherein the toothbrush member may be readily removed and exchanged.

2. Discussion of the Relevant Art

It has been established that significant benefits are derived from regular dental care performed in the home by the individual himself together with periodic examination and treatment by professionally trained dentists. It is universally recognized, for example, that regular brushing of the teeth, particularly after every meal, serves to dislodge food particles which ordinarily are retained adjacent the teeth and which, if allowed to remain, would cause decay and dental caries. When properly administered, regular brushing also services to maintain good circulation in gingival tissue, thereby lessening the likelihood of gingival disease, one of the prime causes of premature loss of teeth. Perhaps of less, but nevertheless significant, importance are the stain removal and brightening actions resulting from regular brushing, which contribute noticeably to the appearance of the individual.

The present invention has found that, when applied under proper control to tooth and gingival surfaces in the human mouth, ultrasonic energy may be successfully employed for regular oral hygienic care without any damage to tooth surfaces or gingival tissues. These ultrasonic cleaning techniques provide a significantly increased cleaning ability, particularly in the interproximal and gum line areas where presently known brushing techniques are inadequate. Briefly, in accordance with the present invention, a cleaning member, which preferably includes a plurality of individual cleaning elements, such as the bristles on a brush, is vibrated at an ultrasonic rate and manually moved over tooth and gingival surfaces under relatively light pressure.

Although not necessarily limited thereto, the combined ultrasonic and manual movement of the cleaning member may be performed in the presence of a fluid, such as water added specifically for the purpose, or the natural fluids present in the human mouth and in the presence of the usual dentifrices such as toothpaste and tooth powder. The unique properties displayed at the tips of an ultrasonically vibrating member such as a brush, enable greatly improved cleaning results to be achieved, particularly in areas where manual or conventional motor driven toothbrushes cannot reach. The ultrasonic energy is applied to the tooth and gingival surfaces such that no damage whatsoever to the surfaces will result. On the other hand, because of the greatly improved cleaning power, the buildup of tartar and scale deposits in the interproximal and gingival areas is significantly lessened, promoting a much higher degree of dental health than is possible with ordinary methods of dental hygienic care.

The art includes many different devices designed specifically to provide a means for dislodging food particles which may be retained between the teeth or removing deposits of plaque, tartar and scale occurring on the teeth. Different types of ultrasonic toothbrushes are known in the prior art. However, it appears that none of the devices in the prior art utilize an ultrasonic driving motor, that is a motor having vibratory output energy between 10,000 and 50,000 Hz that are capable of transferring this ultrasonic vibratory force to the appliance such as a toothbrush or other element, that is the utilizer of this energy, without permanently affixing the magnetostrictive or crystal component to the appliance or permitting ready interchangeability of the toothbrush of other element.

Thus, when it becomes necessary to exchange the appliance, such as a toothbrush, so that different individuals utilizing the apparatus may readily utilize their own toothbrush, it was necessary to change the toothbrush together with the magnetostrictive component, which formed a unitary sub-assembly. This was the only way that the vibratory forces could be transferred from the ultrasonic power source to the toothbrush or other instrument. Certain instruments designed for use by professionals, such as a dentist in the cleaning of the teeth, could be removed with the aid of a tool or by multiple rotations of the instrument. Numerous revolutions were required so that the threads, utilized to couple the instrument to the vibratory power source, could be disengaged. Replacement of the dental instrument occurred only when the instrument became defective or worn out and thus, did not occur very often. However, for individuals to use an ultrasonic toothbrush they must be able to exchange the toothbrush element with ease and a minimal amount of force. Young children must be able to exchange the toothbrush element with ease if the apparatus is to become popular.

Heretofore, one was not able to couple the vibratory energy to the toothbrush or other element, with any degree of success, because the coupling between the magnetostrictive component and the utilizing element required a solid, if not permanent, contact between the two in order to permit the transfer of energy from one to the other. This accounts for the approaches utilized in the prior art, whereby the magnetostrictive component was always affixed to the using element and when the element was replaced the magnetostrictive component was replaced with it as a unitary assembly.

The instant invention overcomes the shortcomings known in the prior art by providing a sealed ultrasonic power source to which an element such as a toothbrush may be quickly connected and disconnected by a unique coupling method.

Therefore, it is an object of the present invention to provide a simple, efficient, reliable means of transferring ultrasonic energy from a power source to a using element.

It is another object of the present invention to provide a quick disconnect coupling suitable for use with an ultrasonic power source.

It is yet another object of the present invention to provide a quick disconnect coupling for use with an ultrasonic power source that is efficient and is capable of transferring the vibratory energy from the power source to the using element.

An ultrasonic toothbrush apparatus, according to the principle of the present invention comprises, in combination, an exchangeable toothbrush member, an ultrasonic power member apparatus for suppling vibratory energy in the ultrasonic range and a coupling arrangement for removing the exchangeable toothbrush member from the ultrasonic power member with less than one complete revolution with a relatively small separating force therebetween.

An ultrasonic toothbrush apparatus comprises, in combination an exchangeable toothbrush member which includes an elongated body portion having an oral contact portion, extending outwardly from one distal end of the body portion. The other end of the body portion is hollow and is provided with a centrally disposed opening terminating in a contact surface. At least one inwardly extending protrusion is disposed at the circumference of the centrally disposed opening to function as a keying guide means. A plurality of threads divided into at least two sections are disposed within the hollow body portion between the contact surface and the opening. The threaded hollow body portion is adapted to receive a mating threaded portion.

An ultrasonic power member supplies the vibratory energy in the ultrasonic range for the exchangeable toothbrush and includes, an elongated housing having an ultrasonic power source for supplying the vibratory energy disposed within the hollow housing. The power source is adapted to be connected to a source of electrical energy and is provided with a vibratory output end, which extends longitudinally at one end of the housing. The longitudinally outwardly extending portion is provided with a plurality of threads divided into at least two sections. A longitudinal channel extends from one distal edge of the extending portion towards the other end of the extending portion terminating in a connecting relatively short channel disposed transverse to the longitudinal channel. The housing outwardly extending portion and the channel are adapted to cooperate with each other so that the hollow body threads and the housing extending portion threads engage. The hollow body inwardly extending protrusion slidably engages the housing elongated member channel so that when the toothbrush member is rotated with respect to the power member housing sufficient for the housing internally extending protrusion to be seated into the relatively short transverse channel, the body portion contact surface is in intimate contact with the distal edge of the housing extending portion, wherein vibratory energy from the ultrasonic power source is efficiently transferred to the toothbrush body portion.

The foregoing and other objects and advantages will appear from the description to follow. In the description, reference is made to accompanying drawing which forms a part hereof, and in which is shown, by way of illustration, a specific embodiment in which the invention may be practiced. This embodiment will be described in sufficient detail to enable those skilled in the art to practice the invention, and that it is to be understood that other embodiments may be utilized and that structural changes may be made without departing from the spirit and scope of the invention. The following detailed description is, therefore, not to be taken in a limiting sense, and the scope of the present invention is best defined by the appended claims.

In the drawings, like reference characters have been utilized to designate like or corresponding components in the alternative embodiments of the invention in order to better understand the invention.

BRIEF DESCRIPTION OF THE DRAWINGS

In order that the invention may be more fully understood, it will now be described, by way of example, with reference to the accompanying drawing in which.

DESCRIPTION OF THE PREFERRED EMBODIMENTS

Figure 1:
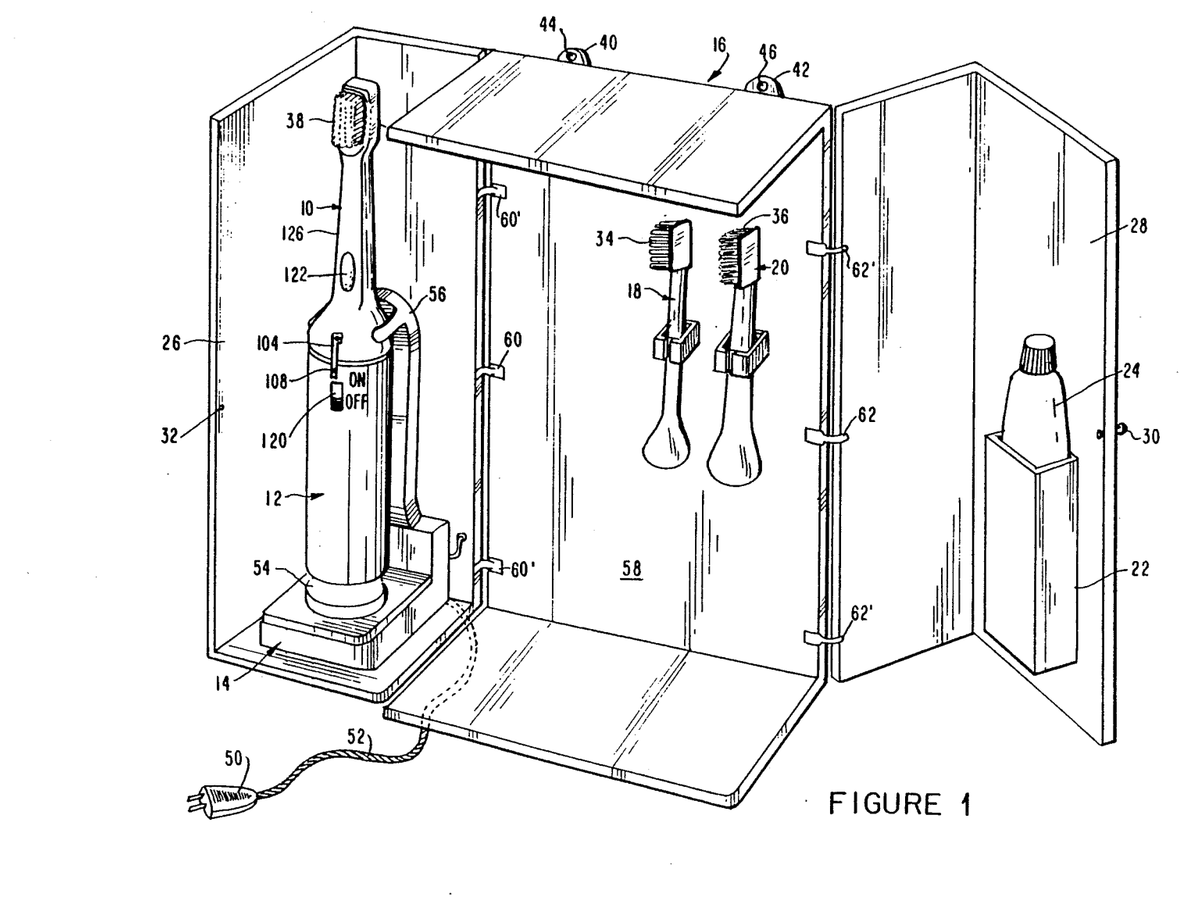
FIG. 1 is a pictorial representation of an ultrasonic toothbrush housing with a plurality of brush members retained in a display case together with the ultrasonic power member or handle, according to the principles of the present invention.

Referring now to the FIGS., and in particular, to FIG. 1, there is shown an ultrasonic toothbrush 10 disposed upon an ultrasonic power member or handle 12 nested on a recharging base member 14 in an open display case 16 that also includes additional toothbrush elements 18 and 20 and a receptacle 22 for a tube of toothpaste 24. Display case 16 is provided with two hinged doors 26 and 28 which when closed are retained in the closed position by a protruding plug member 30 provided on door 28 which is received by aperture 32 provided on door 26. Although only three toothbrushes are shown in FIG. 1, it is apparent that any number of toothbrushes may be provided as needed. Toothbrush 18 may be comprised of a resilient material 34 in lieu of the bristles 36 and 38 provided on brushes 20 and 10, respectively. A resilient material may be provided on toothbrush 18 so that the same power member 12 may be utilized for massaging the gums as may be necessary. The display case 16 is provided with a pair of mounting ears 40 and 42 having apertures 44 and 46 disposed therein, respectively to enable readily mounting to a flat vertical surface, not shown.

Recharging base 14 includes therein a converting circuit arrangement 48, known in the art. The converting circuit arrangement 48 utilizes the A.C. power obtained from a conventional wall outlet, not shown, and is connected thereto, via a plug 50 and line cord 52. Converting circuit 48 rectifies an changes the A.C. voltage appearing at the wall outlet to a D.C. charging voltage for the rechargeable battery 54 disposed in the power member 12. As long as the power member 12 is positioned on the base member 14 and plug 50 is plugged into a standard electrical outlet, battery 54 is trickle charged so that it maintains its peak voltage, which is a relatively low D.C. voltage preferably 9 to 12 volts.

Base member 14 is also provided with an upwardly extending arm 56, which firmly holds the ultrasonic toothbrush and power member in position on the recharging base member 14. Doors 26 and 28 are affixed to rear panel member 58 by a living hinge 60 and 62 or a plurality of conventional hinges 60' and 62'.

Figure 2:
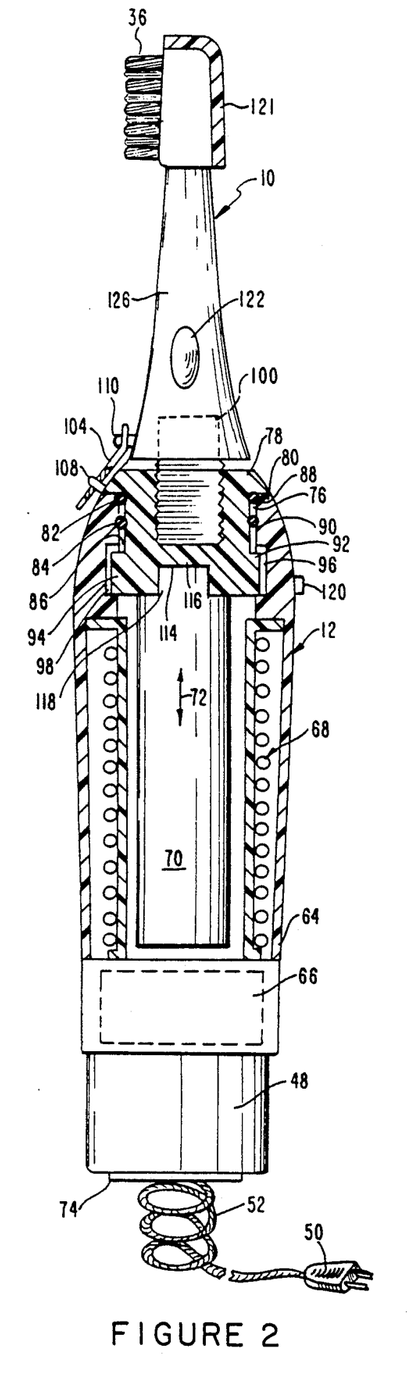
FIG. 2 is an enlarged cross-sectional view of an alternative ultrasonic toothbrush with the toothbrush member in position on the ultrasonic power member or handle suitable for connection to an electrical outlet.
Figure 3:
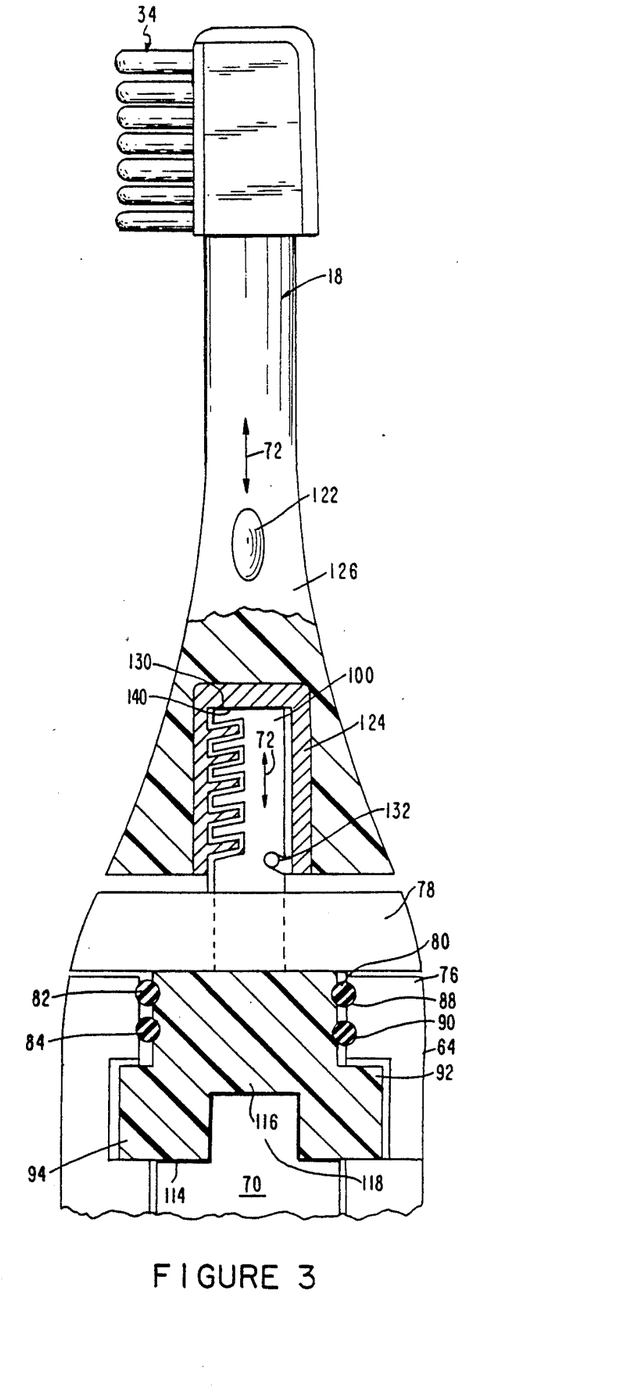
FIG. 3 is a greatly enlarged view partially in cross-section of the toothbrush member in position on the power member.

Referring now to FIGS. 2 and 3, there is shown an enlarged partially cross-sectional view of an alternative ultrasonic power member or handle 12 with an exchangeable toothbrush member 10 disposed thereon. The power member 12 includes in the lower portion of the housing 64, a converting circuit arrangement 48, which is coupled, via line cord 52 and plug 50, to a conventional wall socket, not shown. The converting circuit arrangement 48 is connected to an ultrasonic power source or circuit arrangement 66, known in the art, which provides the driving current for the coil 68 that provides the alternating driving magnetic fields which cause the magnetostrictive element 70 to move in the direction of arrow 72 as the polarity of the driving current appearing in coil 68 changes direction, in a known manner.

The housing 64 has a closed end 74 through which line cord 52 enters and is connected to the converting circuit arrangement as stated earlier. The other end 76 of housing 64 is open and closed or covered with a closure or cap member 78 which is adapted to fit in the opening 80 with clearance space and is provided with a portion that extends over the edge 76 of housing 64. Resilient O-rings 82 and 84, preferably made of a rubber compound, are disposed within the clearance space between the housing and 76 and the circumferential wall of cap member 78 and are fitted within grooves 88 and 90 provided in the housing 64 to maintain them in the proper position. O-rings 82 and 84 function to prevent any fluid from entering into the internal portion of the housing 64 where it may damage or cause corrosion to the coil 68, the power source 66 or the converting circuit arrangement 48.

Cap member 78 is also provided with a pair of extending flanges 92 and 94 which extend outwardly from the circumferential wall 86 and slidably engage channels 96 and 98, respectively provided proximate the open end 76 of housing 64 enabling the cap member 78 to move in a linear direction as shown by arrow 72 resisting any rotary movement. Therefore, the flanges 92 and 94 will keep the cap member 78 in position when any rotary forces are applied.

Figure 7:
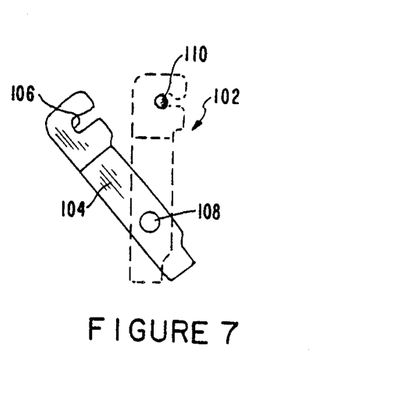
FIG. 7 is a top plan view of a locking device for insuring that the toothbrush member and the power member remain properly engaged in use.

Cap member 78 may also be provided with a locking device 102 which includes a pivot arm 104 (see FIG. 7) and a keyhole type aperture 106 adapted to rotate about a pivot axis 108 which is configured to retain outwardly extending pin 110 which may be provided on elongated body portion 126 of toothbrush 10.

Cap member 78 is permanently affixed, preferably by means of epoxy 114 provided on the common surfaces between the magnetostrictive component 70 and the lower portion 116 of cap member 78 and the outward end portion 118 magnetostrictive component 70. Thus, the magnetostrictive component 70 of the ultrasonic power source 66 is never required to leave or be taken out of the housing 64 of the power member 12. An on-off or power switch 120 is provided on the housing 64 and when it is placed in the "on" position the power source 66 causes the output ultrasonic vibratory energy to be generated.

Toothbrush 10 is also provided with a resilient hood 121 to insulate from acoustical vibrations and with a thumb depression 122 to enable the user thereof to apply thumb pressure for the rotary motion required and the linear force necessary to remove brush 10 from the power member 12 when desired and conveniently allows the user to apply the rotary motion and pressure necessary to attach the toothbrush 10 to the power member 12.

Figures 4, 5:
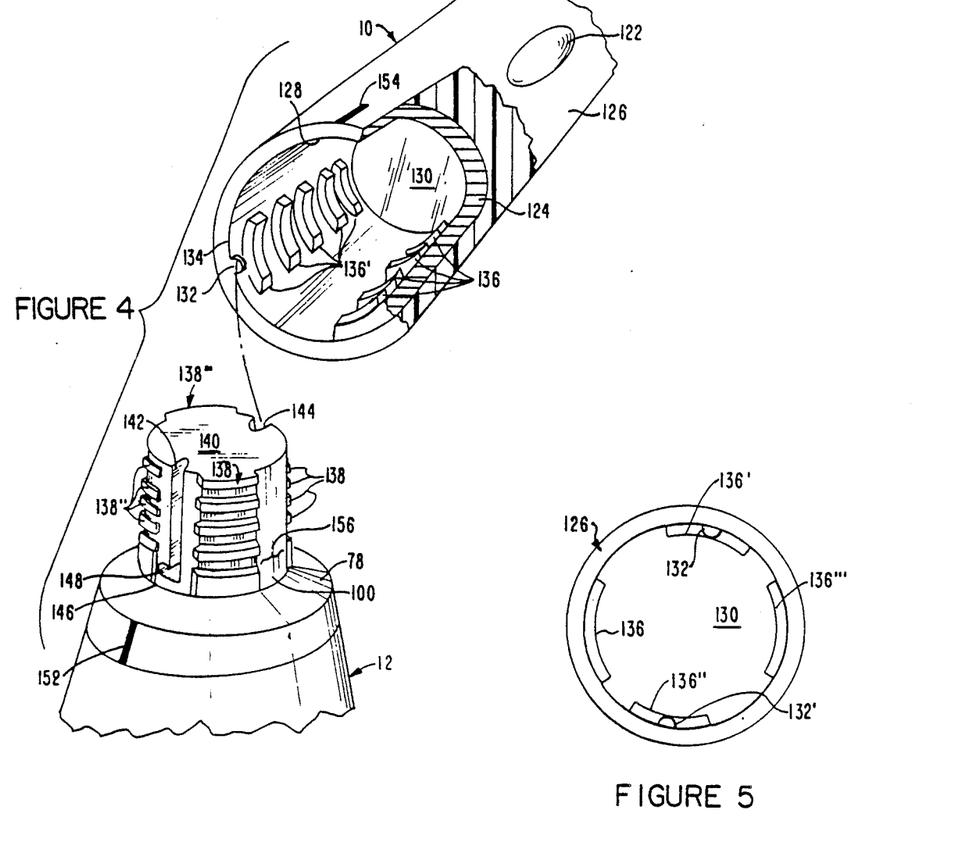
FIG. 4 is a partial, exploded view of the lower portion of an exchangeable toothbrush member removed from the ultrasonic power member revealing the coupling configuration.
FIG. 5 is a bottom view of the elongated body portion of the toothbrush of FIG. 4.

Referring now to FIG. 3, there is shown in a greatly enlarged view of the toothbrush 18 affixed on the cap member 78 in position for operation. Although the drawings in one embodiment show that the longitudinally outwardly extending portion 100 of cap member 78 may be fabricated from two separate components; e.g., the cap member being plastic and the longitudinally outwardly extending portion being fabricated from metal and affixed in the cap member in a conventional manner (epoxy). The cap member 78 is also shown as being fabricated from a single unitary material such as Lexan as shown in FIG. 4, which is equally suitable for the present application. It is also to be noted that the toothbrush 18 may have a metal insert 124 affixed therein, in a conventional manner such as by epoxy. It also may be fabricated as a single integral piece made from Lexan as is the remaining portion of the toothbrush 18.

Referring now specifically to FIG. 4, there is shown an exploded view of the toothbrush 10 which has an elongated body portion end 126 that is hollow, being provided with a centrally disposed opening 128, terminating in a contact surface 130 to which the majority of the ultrasonic energy is to be applied. Inwardly extending protrusions 132 and 132' are disposed at the circumference 134 of the opening 128 and in line with the threads 136' and 136", respectively. The protrusions 132 and 132' function as keying guides as will be explained hereinafter.

Figure 6:
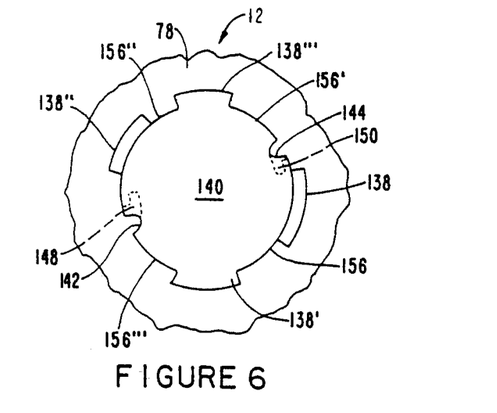
FIG. 6 is a top view of the handle or power member of FIG. 4.

A plurality of threads 136, 136' and 136" are divided into at least two sections, preferably four sections, and are disposed within the hollow body portion 126 of toothbrush 10 between the contact surface 130 and the circumferential surface edge 134. The threaded hollow body portion 126 or metal insert 124 is adapted to receive a mating threaded portion 100 as will be explained hereinafter. The cap member 78, as explained earlier is provided with a longitudinally outwardly extending portion 100 which is provided with a plurality of threads 138 divided into at least two sections, preferably four sections, 138, 138', 138" and 138"' which are adapted to cooperate with and mate with complimentary threads 136, 136', 136" and 136"' for a tight fit so that the distal edge 140 of the outwardly extending portion 100 is in intimate forceful contact with contact surface 130 of the elongated body portion 126. A pair of longitudinally disposed channels 142 and 144 extend from the distal edge 140 of the outwardly extending portion 100 of cap member 78 towards the other end 146 of the outwardly extending portion and terminates in relatively short channels 148 and 150 which are disposed transverse or perpendicular to channels 142 and 144 (see FIG. 6).

Indicia 152 may be provided on cap member 78 to indicate when the toothbrush 10 is firmly in position and locked when the corresponding indicia 154 provided on the toothbrush 10 is in alignment with the indicia 152 provided on the cap member 78.

An end view of the hollow elongated body portion 126 showing the arrangement of the threads 136, 136', 136" and 136"' may be seen in FIG. 5.

In operation, the elongated body portion 112 or 126 may be inserted onto the power member or handle 12 by aligning the protrusions 132 and 132' with channels 144 and 142, respectively, exerting a slight pressure thereon. Threads 136, 136', 136" and 136"' will be in position to move in the spaces 156, 156', 156" and 156"' between each of the thread segments provided on the extending portion 100. By exerting a small amount of pressure the protrusion 132 and 132' will be seated at the end of grooves 142 and 144 and with a slight rotational force protrusions 132 and 132' will enter into transverse channels 148 and 150 at the same time engaging threads 138, 138', 138", and 138'" by threads 136, 136', 136" and 136'", thus providing intimate contact between surfaces 140 and 130 and causing the alignment indicia 152 and 154 to indicate when the toothbrush 10 is seated in its home or operating position. If a locking means is also used it then may engage a pin 110 extending outwardly and in line with protrusions 132 and 132' thereby providing a further means to insure that the toothbrush 10 is securely engaged on the power member or handle 12.

Removal of the exchangeable toothbrush 10 may be accomplished by reversing the procedure, releasing the locking means 102 and then exerting a small rotational force to cause the protrusions 132 and 132' to leave the transverse grooves 148 and 150 and enter into channels 142 and 144 and then applying a longitudinal force to separate the two members.

It is also to be noted that the male or extending portion 100 may be provided on the toothbrush element 10 and the female or hollow opening 126 may be provided on the closure or cap member 78 and/or the power handle 12 as is well known by those knowledgeable in the art. This alternative embodiment will provide the same desired results as discussed above.

Hereinbefore has been disclosed an ultrasonic toothbrush apparatus capable of being exchanged with another unit with a minimum of effort and force. It will be understood that various changes in the details, materials, arrangement of parts and operating conditions which have been hereinbefore described and illustrated in order to explain the nature of the invention may be made by those skilled in the art within the principles and scope of the instant invention.

Having thus set forth the nature of the invention what is claimed is:

1. An ultrasonic toothbrush apparatus comprising, in combination:
   A. an exchangeable toothbrush member including;
      (i) an elongated body portion having an oral contact portion extending outwardly from one distal end of said body portion,
      (ii) the other end of said body portion being hollow and provided with a centrally disposed opening terminating in a contact surface,
      (iii) at least one inwardly extending protrusion being disposed at the circumference of said centrally disposed opening to function as a keying guide means,
      (iv) a plurality of threads divided into at least two sections disposed within said hollow body portion between said contact surface and said opening, said threaded hollow body portion being adapted to receive a mating threaded portion; and
   B. an ultrasonic power member means for supplying vibratory energy in the ultrasonic range including;
      (i) an elongated housing having an ultrasonic power source for supplying vibratory energy in the ultrasonic range disposed within said housing, said power source being adapted to be connected to a source of electrical energy and having a vibratory output end longitudinally extending at one end of said housing,
      (ii) said one end having a distal edge and a longitudinally outwardly extending portion provided with a plurality of mating threads divided into at least two sections, and
      (iii) a longitudinal channel extending from said distal edge of said one end extending portion towards the other end of said extending portion terminating in a connecting relatively short channel disposed transverse to said longitudinal channel,
   wherein, when said hollow body portion threads and said housing extending portion mating threads engage, and said hollow body inwardly extending protrusion slidably engages said housing elongated member channel when said toothbrush member is rotated with respect to said power member means housing sufficient for said housing internally extending protrusion to be seated into said relatively short transverse channel, said body portion contact surface is in intimate contact with said distal edge of said housing extending portion, thereby efficiently transferring said vibratory energy from said ultrasonic power source to said toothbrush body portion.

2. An ultrasonic toothbrush according to claim 1 further including locking means, said locking means being disposed on said housing, said toothbrush body portion being provided with an outwardly extending protrusion in alignment with said inwardly extending protrusion adapted to be engaged by said locking means when said body portion contact surface is in intimate contact with the distal edge of said housing extending portion.

3. An ultrasonic toothbrush according to claim 1 further including restraining means for preventing said vibratory output end from rotating when said toothbrush body portion is rotated.

4. An ultrasonic toothbrush according according to claim 3 wherein said restraining means is provided by a longitudinal outwardly extending portion provided on said vibratory output end which is adapted to cooperate with and slidably engage a longitudinal channel provided on said power member means housing.

5. An ultrasonic toothbrush according to claim 1 wherein said oral contact portion includes a plurality of bristles.

6. An ultrasonic toothbrush according to claim 1 wherein said oral contact portion includes a resilient material.

7. An ultrasonic toothbrush according to claim 1 wherein said plurality of threads are divided into three sections equally spaced about the circumference of said body portion opening.

8. An ultrasonic toothbrush according to claim 1 wherein said plurality of threads are divided into four sections equally spaced about the circumference of said body portion opening.

9. An ultrasonic toothbrush according to claim 1 further including resilient sealing means disposed between said housing and said ultrasonic power source for preventing moisture and water from entering said housing.

10. An ultrasonic toothbrush according to claim 9 wherein said sealing means comprises at least one O-ring member.

11. An ultrasonic toothbrush according to claim 1 wherein said ultrasonic power source comprises:
    A. a relatively low voltage rechargeable battery means, B. electrical circuit means for providing said vibratory ultrasonic energy connected to said battery means.

12. An ultrasonic toothbrush according to claim 1 wherein said ultrasonic power source comprises converter means for converting said source of electrical to a relatively low D.C. voltage for operating said ultrasonic power source.

13. A ultrasonic toothbrush apparatus according to claim 1 wherein said elongated member is a single unitary element.

14. An ultrasonic toothbrush apparatus comprising:
A. an exchangeable toothbrush member;
B. an ultrasonic power member means for supplying vibratory energy in the ultrasonic range having said toothbrush member removably affixed thereon; and
C. means for removing said exchangeable toothbrush member from said ultrasonic power member means with less than one complete revolution and a relatively small separating force therebetween, said means including at least two threaded circumferentially spaced sections having a plurality of threads in each said member and said member means.

15. An ultrasonic toothbrush according to claim 14 wherein said exchangeable toothbrush member includes;
(i) an elongated body portion having an oral contact portion extending outwardly from one distal end of said body portion,
(ii) the other end of said body portion being hollow and provided with a centrally disposed opening terminating in a contact surface,
(iii) at least one inwardly extending protrusion being disposed at the circumference of said centrally disposed opening to function as a keying guide means,
(iv) said plurality of threads having divided into at least two sections disposed within said hollow body portion between said contact surface and said opening, said threaded hollow body portion being adapted to receive a mating threaded portion; and
said ultrasonic power member means includes;
(i) an elongated hollow housing having an opening at one end,
(ii) an ultrasonic power source for supplying vibratory energy in the ultrasonic range disposed within said hollow housing, said power source being adapted to be connected to a source of electrical energy and having a vibratory output end longitudinally extending towards said housing opening,
(iii) a longitudinally outwardly extending portion having a distal edge and provided with a plurality of mating threads divided into at least two sections extending through said housing opening, and
(iv) a longitudinal channel extending from said distal edge of said extending portion towards the other end of said extending portion terminating in a connecting relatively short channel disposed transverse to said longitudinal channel,
wherein, when said hollow body portion threads and said extending portion mating threads engage, and said hollow body inwardly extending protrusion slidably engages said extending portion channel so that when said toothbrush member is rotated with respect to said power member means housing sufficient for said housing internally extending protrusion to be seated into said relatively short transverse channel, said body portion contact surface is in intimate contact with said distal edge of said extending portion, so that vibratory energy from said ultrasonic power source is efficiently transferred to said toothbrush body portion.

16. An ultrasonic toothbrush according to claim 15 further including locking means for retaining said toothbrush body portion upon said housing when said toothbrush body portion is receiving vibratory energy, said locking means being disposed on said housing, said toothbrush body portion being provided with an outwardly extending protrusion in alignment with said inwardly extending protrusion adapted to be engaged by said locking means when said body portion contact surface is in intimate contact with the distal edge of said extending portion.

17. An ultrasonic toothbrush according to claim 15 further including restraining means for preventing said vibratory output end from rotating when said toothbrush member body portion is receiving vibratory energy.

18. An ultrasonic toothbrush according according to claim 17 wherein said restraining means is provided by a longitudinal outwardly extending portion provided on said vibratory output end which is adapted to cooperate with and slidably engage a longitudinal channel provided on said power member means housing.

19. An ultrasonic toothbrush according to claim 15 wherein said plurality of threads are divided into three sections equally spaced about the circumference of said body portion opening.

20. An ultrasonic toothbrush according to claim 15 further including resilient sealing means disposed between said housing and said ultrasonic power source for preventing moisture and water from entering said housing opening.

21. An ultrasonic toothbrush according to claim 20 wherein said sealing means comprises at least one O-ring member.

22. An ultrasonic toothbrush apparatus according to claim 15 wherein said elongated member is a single unitary element.

23. A quick release ultrasonic connector for releasably connecting a member to a source of vibratory ultrasonic energy comprises:
(i) an elongated body portion having an element disposed on one distal end of said body portion,
(ii) the other end of said body portion being hollow and provided with a centrally disposed opening terminating in a contact surface,
(iii) at least one inwardly extending protrusion being disposed at the circumference of said centrally disposed opening to function as a keying guide means,
(iv) a plurality of threads divided into at least two sections disposed within said hollow body portion between said contact surface and said opening, said threaded hollow body portion being adapted to receive a mating threaded portion; and
said source of ultrasonic power energy includes;
(i) an elongated hollow housing having an ultrasonic power motor means for supplying vibratory energy in the ultrasonic range disposed within said hollow housing, said power source being adapted to be connected to a source of electrical energy and having a vibratory output end longitudinally extending at one end of said housing, (ii) a longitudinally outwardly extending portion having a distal edge and provided with a plurality of mating threads divided into at least two sections at said one end, and (iii) a longitudinal channel extending from said distal edge of said housing one end extending portion extends towards the other end of said extending portion terminating in a connecting relatively short channel disposed transverse to said longitudinal channel, wherein, when said hollow body portion threads and said housing extending portion mating threads engage, and said hollow body inwardly extending protrusion slidably engages said housing elongated member channel so that when said element is rotated with respect to said power motor housing sufficient for said housing internally housing extending protrusion to be seated into said relatively short transverse channel said body portion contact surface is in intimate contact with said distal edge of said housing extending portion, so that vibratory energy from said ultrasonic power source is efficiently transferred to said element.

24. An ultrasonic toothbrush according to claim 23 further including locking means, said locking means being disposed on said housing, said element body portion being provided with an outwardly extending protrusion in alignment with said inwardly extending protrusion adapted to be engaged by said locking means when said body portion contact surface is in intimate contact with the distal edge of said extending portion.

25. An ultrasonic toothbrush apparatus comprising, in combination:

A. an exchangeable toothbrush member including;
 (i) an elongated body portion having an oral contact portion extending outwardly from one distal end of said body portion,
 (ii) the other end of said body portion provided with a centrally disposed connector portion terminating in a contact surface,
 (iii) at least one protrusion being disposed at the circumference of said centrally disposed connector portion to function as a keying guide means,
 (iv) a plurality of threads divided into at least two sections disposed on said connector portion between said contact surface and the distal edge of said body portion other end, said threaded connector portion being adapted to receive a mating connector threaded portion; and B. an ultrasonic power member means for supplying vibratory energy in the ultrasonic range including;
 (i) an elongated housing having an ultrasonic power source for supplying vibratory energy in the ultrasonic range disposed within said housing, said power source being adapted to be connected to a source of electrical energy and having a vibratory output end longitudinally extending towards one end of said housing,
 (ii) a mating connector portion affixed on said vibratory output end, said mating connector portion having,
  a. a longitudinally extending portion having a distal edge and provided with a plurality of threads divided into at least two sections, and
  b. a longitudinal channel extending from said distal edge of said mating connector portion towards the other end of said mating connector portion terminating in a relatively short channel disposed transverse to said longitudinal channel, said mating connector portion and said connector portion being adapted to cooperate with each other so that said connector portion threads and said mating connector portion threads engage and said connector portion protrusion slidably engages said mating connector channel so that when said toothbrush member is rotated with respect to said power member means housing sufficient for said connector portion protrusion to be seated into said relatively short transverse channel said connector portion contact surface is in intimate contact with said distal edge of said mating connector portion, wherein vibratory energy from said ultrasonic power source is efficiently transferred to said toothbrush body portion.

26. An ultrasonic toothbrush according to claim 25 further including locking means, said locking means being disposed on said mating connector portion, said connector portion being provided with an outwardly extending protrusion in alignment with said connector portion protrusion adapted to be engaged by said locking means when said connector portion contact surface is in intimate contact with the distal edge of said mating connector portion.

27. An ultrasonic toothbrush according to claim 25 wherein said toothbrush member further includes finger grip means for ease in rotating said toothbrush body portion with respect to said power member means housing.

28. An ultrasonic toothbrush according to claim 25 further including restraining means for preventing said mating connector portion vibratory output end from rotating when said connector portion is rotated.

29. An ultrasonic toothbrush according according to claim 28 wherein said restraining means is provided by a longitudinal outwardly extending portion provided on said vibratory output end which is adapted to cooperate with and slidably engage a longitudinal channel provided on said power member means housing.

30. An ultrasonic toothbrush according to claim 25 wherein said connector portion is female and said mating connector portion is male.

31. An ultrasonic toothbrush according to claim 25 wherein said plurality of threads are divided into three sections equally spaced about the circumference of said body portion opening.

32. An ultrasonic toothbrush according to claim 25 wherein said plurality of threads are divided into four sections equally spaced about the circumference of said body portion opening.

33. An ultrasonic toothbrush according to claim 25 further including resilient sealing means disposed between said mating connector portion and said housing for preventing moisture and water from entering said housing opening.

34. An ultrasonic toothbrush according to claim 33 wherein said sealing means comprises at least one O-ring member.

35. An ultrasonic toothbrush apparatus comprising, in combination:

A. an exchangeable toothbrush member including;
 (i) an elongated body portion having an oral contact portion extending outwardly from one distal end of said body portion, (ii) the other end of said body portion being provided with a centrally disposed opening terminating in a contact surface, (iii) a plurality of threads divided into at least two sections disposed on said body portion proximate said contact surface, said threaded body portion being adapted to receive a mating threaded portion; and B. an ultrasonic power member means for supplying vibratory energy in the ultrasonic range including;

(i) an elongated housing having an ultrasonic power source for supplying vibratory energy in the ultrasonic range disposed within said housing, said power source being adapted to be connected to a source of electrical energy and having a vibratory output at one end of said housing, (ii) a longitudinally outwardly extending portion having a distal edge and a plurality of mating threads divided into at least two sections provided at said one end, wherein, when said body threads and said housing extending portion threads engage and said toothbrush member is rotated with respect to said power member means housing sufficient for said body portion contact surface to be in intimate contact with said distal edge of said housing extending portion, vibratory energy from said ultrasonic power source is efficiently transferred to said toothbrush body portion.

36. An ultrasonic toothbrush according to claim 35 further including locking means, said locking means being disposed on said housing, said toothbrush body portion being provided with an outwardly extending protrusion in alignment with said inwardly extending protrusion adapted to be engaged by said locking means when said body portion contact surface is in intimate contact with the distal edge of said housing extending portion.

37. An ultrasonic toothbrush according to claim 35 further including restraining means for preventing said vibratory output end from rotating when said toothbrush body portion is rotated.

38. A quick release ultrasonic connector for releasably connecting a member to a source of vibratory ultrasonic energy comprises:

(i) an elongated body portion having an element disposed on one end thereof, (ii) the other end of said body portion terminating in a centrally disposed contact surface, (iii) a plurality of threads divided into at least two sections disposed upon said body portion between said contact surface and said one end, said threaded body portion being adapted to receive a mating threaded portion; and said source of ultrasonic vibratory energy includes;

(i) an elongated housing having an ultrasonic power motor means for supplying vibratory energy in the ultrasonic range disposed within said housing, said power source being adapted to be connected to a source of electrical energy and a vibratory output at one end of said housing, (ii) a longitudinally outwardly extending portion having a distal edge and a plurality of mating threads divided into at least two sections at said one end, wherein, when said body portion threads and said housing extending portion mating threads engage, and said element is rotated with respect to said power motor housing sufficient for said body portion contact surface to be in intimate contact with said distal edge of said housing extending portion vibratory energy from said ultrasonic power source is efficiently transferred to said element.

39. An ultrasonic toothbrush according to claim 38 further including locking means, said locking means being disposed on said housing, said element body portion being provided with an outwardly extending protrusion in alignment with said inwardly extending protrusion adapted to be engaged by said locking means when said body portion contact surface is in intimate contact with the distal edge of said extending portion.

* * * * *